US012699066B2

(12) United States Patent
Wu et al.

(10) Patent No.: US 12,699,066 B2
(45) Date of Patent: Aug. 4, 2026

(54) ADJOINT AUTOMATIC MONITORING DEVICE AND METHOD FOR DEPOSITION RATE OF SALT MIST

(71) Applicant: SOUTHWEST TECHNICAL ENGINEERING RESEARCH INSTITUTE OF CHINA SOUTH INDUSTRIES GROUP, Chongqing (CN)

(72) Inventors: Hulin Wu, Chongqing (CN); Qiongyao He, Chongqing (CN); Yuanyao Cen, Chongqing (CN); Yao Wu, Chongqing (CN); Fangchao Zhao, Chongqing (CN); Kun Zhou, Chongqing (CN)

(73) Assignee: SOUTHWEST TECHNICAL ENGINEERING RESEARCH INSTITUTE OF CHINA SOUTH INDUSTRIES GROUP, Chongqing (CN)

( * ) Notice: Subject to any disclaimer, the term of this patent is extended or adjusted under 35 U.S.C. 154(b) by 152 days.

(21) Appl. No.: 18/569,530

(22) PCT Filed: Jun. 30, 2023

(86) PCT No.: PCT/CN2023/104362
§ 371 (c)(1),
(2) Date: Dec. 12, 2023

(87) PCT Pub. No.: WO2025/000417
PCT Pub. Date: Jan. 2, 2025

(65) Prior Publication Data
US 2025/0231136 A1    Jul. 17, 2025

(30) Foreign Application Priority Data
Jun. 29, 2023    (CN) ......................... 202310779024.0

(51) Int. Cl.
*G01N 27/27* (2006.01)
*G01N 17/02* (2006.01)
(Continued)

(52) U.S. Cl.
CPC ............. *G01N 27/27* (2013.01); *G01N 17/02* (2013.01); *G01N 27/333* (2013.01); *G01N 27/4166* (2013.01); *G01N 33/182* (2013.01)

(58) Field of Classification Search
CPC .... G01N 27/27; G01N 27/333; G01N 27/403; G01N 27/416; G01N 27/4166; G01N 33/182; G01N 17/02
See application file for complete search history.

(56) References Cited

FOREIGN PATENT DOCUMENTS

CN        113030190 A      6/2021
CN        113447539 A      9/2021
(Continued)

OTHER PUBLICATIONS

ASTM International Designation: G140-02 (Reapproved 2019), "Standard Test Method for Determining Atmospheric Chloride Deposition Rate by Wet Candle Method . . . " (Year: 2019).*
(Continued)

*Primary Examiner* — Alexander S Noguerola
(74) *Attorney, Agent, or Firm* — Suiter Swantz IP

(57) ABSTRACT

The present disclosure provides an adjoint automatic monitoring device and method for a deposition rate of salt mist. The adjoint automatic monitoring device includes: a wet candle method-based salt mist deposition rate acquisition unit, a single chip, a digital-to-analog (D/A) conversion circuit, and a data acquisition module. According to the present disclosure, a current value and a height variation of a solution in a trapping pool of the wet candle method-based salt mist deposition rate acquisition unit are acquired by the data acquisition module, and then the deposition rate of salt
(Continued)

mist is calculated by the single chip. Real-time online monitoring of the deposition rate of salt mist is realized.

10 Claims, 9 Drawing Sheets

(51) Int. Cl.
| | | |
|---|---|---|
| *G01N 27/333* | (2006.01) | |
| *G01N 27/416* | (2006.01) | |
| *G01N 33/18* | (2006.01) | |

(56) References Cited

FOREIGN PATENT DOCUMENTS

| CN | 113970579 A | 1/2022 |
|---|---|---|
| CN | 114384123 A | 4/2022 |
| CN | 115493981 A | 12/2022 |
| CN | 116297126 A | 6/2023 |
| JP | 2014038026 A | 2/2014 |

OTHER PUBLICATIONS

U.S. Department of Commerce National Technical Information Service AD-A020 110, J. R. Sprouse, "An Improved Analytical Method for Atmospheric Chlorides in Tropic Tests," Army Tropic Test Center, Jul. 1975 (Year: 1975).*

ASTM D512: Standard Test Methods for Chloride Ion in Water, the title and Test Method C-Ion-Selective Electrode, sections 22-29, Designation: D 512-89 (Reapproved 1999) (Year: 1999).*

The Electrochemical Society Electrochemistry Dictionary and Encyclopedia, 2025, https://knowledge.electrochem.org/ed/dict.htm#e20 (Year: 2025).*

EPO machine-generated English language translation of CN 116297126A, patent published Jun. 23, 2023 (Year: 2023).*

Wolfram Mathworls—Common logarithm, 2025, https://mathworld.wolfram.com/CommonLogarithm.html (Year: 2025).*

EPO machine-generated English language translation of CN 113970579 A, patent published Jan. 25, 2022 (Year: 2022).*

EPO machine-generated English language translation of CN 115493981 A, patent published Dec. 26, 2022 (Year: 2022).*

Alcantara et al., "Airborne chloride deposit and its effect on marine atmospheric corrosion of mild steel," Corrosion Science, 97, Apr. 28, 2015, 15 pages.

China National Intellectual Property Office, First Office Action received in CN Application No. 202310779024.0, Nov. 1, 2024, 8 pages (including translation).

China National Intellectual Property Office, International Search Report received in CN Application No. PCT/CN2023/104362, Dec. 22, 2023, 8 pages.

Hu et al., "Cl-Sedimentation Rate in Atmosphere of Tropical Island," vol. 29, No. 6, Jun. 2018, 5 pages.

Liu et al., "Crevice Corrosion Behaviors of X70 Pipeline Steel in Tropic Marine Atmosphere," Equipment Environmental Engineering, vol. 14, No. 9, Sep. 30, 2017, 3 pages.

* cited by examiner

ADJOINT AUTOMATIC MONITORING DEVICE AND METHOD FOR DEPOSITION RATE OF SALT MIST

CROSS REFERENCE TO RELATED APPLICATION

This patent application is a national stage application of International Patent Application No. PCT/CN2023/104362, filed on Jun. 30, 2023, which claims the benefit and priority of Chinese Patent Application No. 202310779024.0 filed with the China National Intellectual Property Administration on Jun. 29, 2023, and entitled "ADJOINT AUTOMATIC MONITORING DEVICE AND METHOD FOR DEPOSITION RATE OF SALT MIST", the disclosure of which is incorporated by reference herein in its entirety as part of the present application.

TECHNICAL FIELD

The present disclosure relates to the technical field of environmental monitoring, and in particular, to an automatic monitoring device and method for a deposition rate of salt mist.

BACKGROUND

In atmospheric environment, especially in marine atmospheric environment, salt mist in the environment is a major factor that induces corrosion of materials. How to monitor a deposition rate of salt mist in the atmospheric environment is the premise of protecting metallic materials against corrosion.

An existing sampling method for a deposition rate of salt mist is a method of sampling by a dry plate process with a gauze in combination with laboratory analysis. The sampling gauze is exposed to the atmospheric environment to collect a sufficient amount of chloride ion deposition after a 30-60 chloride experiment period. The content of chloride ions in the gauze is then obtained by gas chromatography or chemical analysis, whereby the amount of chloride ion deposition is calculated. Such a method is long in experimental period and cannot realize real-time online monitoring. It is difficult for the method to realize association of natural environment with the deposition rate of salt mist. The method may restrict research on the corrosion mechanism of metallic materials to a certain extent.

SUMMARY

An objective of the present disclosure is to provide an adjoint automatic monitoring device and method for a deposition rate of salt mist to realize real-time online monitoring on a deposition rate of salt mist.

To achieve the above objective, the present disclosure provides the following technical solutions.

The present disclosure provides an adjoint automatic monitoring device for a deposition rate of salt mist, including a wet candle method-based salt mist deposition rate acquisition unit, a single chip, a digital-to-analog (D/A) conversion circuit, and a data acquisition module;

where the single chip is connected to the D/A conversion circuit; the D/A conversion circuit is connected to the wet candle method-based salt mist deposition rate acquisition unit; the single chip is configured to send a digital signal instruction; the D/A conversion circuit is configured to convert the digital signal instruction into an analog signal instruction and send the analog signal instruction to the wet candle method-based salt mist deposition rate acquisition unit;

the data acquisition module is connected to a chloride ion selective electrode of the wet candle method-based salt mist deposition rate acquisition unit and the single chip separately; the data acquisition module is configured to acquire a current value and a height variation output by the wet candle method-based salt mist deposition rate acquisition unit; and the single chip is configured to calculate a deposition rate of salt mist based on the current value and the height variation.

Optionally, the data acquisition module includes a current-to-voltage (I/V) conversion circuit, a two-stage amplifying circuit, and an analog-to-digital (A/D) conversion circuit.

Optionally, the adjoint automatic monitoring device further includes: a device base, a device top cover, a temperature and humidity sensor, a lithium battery pack, a switch, a circular connector, and an organic light-emitting diode (OLED) display module;

where the wet candle method-based salt mist deposition rate acquisition unit is fixed to the device base; a gauze for depositing salt mist in an environment into a solution in the wet candle method-based salt mist deposition rate acquisition unit is exposed to the environment through a through hole formed in the device top cover and covered with a metal mesh enclosure;

the temperature and humidity sensor is disposed on the device top cover;

the lithium battery pack is disposed in the device base, and connected to the wet candle method-based salt mist deposition rate acquisition unit and the data acquisition module;

the switch and the circular connector are both disposed on a sidewall of the device base;

the switch is connected to a power output terminal of the lithium battery pack; the circular connector is connected to the single chip through an RS422 serial port module and configured for connection with an external apparatus; and the OLED display module is disposed on the device top cover and connected to the single chip.

Optionally, the wet candle method-based salt mist deposition rate acquisition unit includes a wet candle, the gauze, a trapping pool, the chloride ion selective electrode, and a liquid level height detection module;

the gauze has one end wound around the wet candle and the other end deposited into the solution in the trapping pool and serves for depositing the salt mist in the environment into the solution;

the chloride ion selective electrode has one end placed deep into the solution in the trapping pool and is configured to sense a current value of the solution in the trapping pool;

the liquid level height detection module is disposed on an outer side of the trapping pool and configured to sense a height variation of the solution in the trapping pool; and the current value and the height variation are used for calculating the deposition rate of salt mist.

Optionally, the trapping pool includes a trapping pool body and a trapping pool top cover;

a sealing ring is disposed between the trapping pool body and the trapping pool top cover;

a taper hole is formed in the trapping pool top cover; and the other end of the gauze passes through the taper hole to be placed into the solution in the trapping pool body.

Optionally, an injection hole is further formed in the trapping pool top cover and sealed with a sealing plug.

Optionally, a formula for calculating the deposition rate of salt mist is as follows:

$$S_d = \frac{m_t - m_0}{At};$$

$$m_t = 35.5 \times 10^{\frac{I_{Cl} - 0.19822}{0.02848}} \times 12 \times (3 - \Delta h);$$

where $S_d$ represents the deposition rate of salt mist, and $m_t$ a mass of chloride ions in the solution in the trapping pool at time t, $m_0$ an initial mass of chloride ions in the solution in the trapping pool, A an exposed surface area of the gauze, $I_{Cl}$ the sensed current value of the solution in the trapping pool, and $\Delta h$ the height variation of the solution in the trapping pool.

An adjoint automatic monitoring method for a deposition rate of salt mist includes the following steps:

arranging a wet candle method-based salt mist deposition rate acquisition unit in an environment to be measured;

acquiring a current value and a height variation of a solution in a trapping pool of the wet candle method-based salt mist deposition rate acquisition unit in real time;

calculating a concentration logarithm of chloride ions of the solution in the trapping pool by using a calibration relationship according to the current value, where the calibration relationship is used for characterizing a relationship between a current and a concentration of chloride ions; and calculating the deposition rate of salt mist based on the concentration logarithm of chloride ions and the height variation of the solution in the trapping pool.

Optionally, the calibration relationship is as follows: $I_{Cl}=0.02848C+0.19822$;

where $I_{Cl}$ represents a sensed current value of the solution in the trapping pool, and C the concentration logarithm of chloride ions.

Optionally, a formula for calculating the deposition rate of salt mist is as follows:

$$S_d = \frac{m_t - m_0}{At};$$

$$m_t = 35.5 \times 10^{\frac{I_{Cl} - 0.19822}{0.02848}} \times 12 \times (3 - \Delta h);$$

where $S_d$ represents the deposition rate of salt mist, and $m_t$ a mass of chloride ions in the solution in the trapping pool at time t, $m_0$ an initial mass of chloride ions in the solution in the trapping pool, A an exposed surface area of the gauze, $I_{Cl}$ the sensed current value of the solution in the trapping pool, and $\Delta h$ the height variation of the solution in the trapping pool.

According to specific embodiments provided in the present disclosure, the present disclosure has the following technical effects:

The present disclosure provides an adjoint automatic monitoring device and method for a deposition rate of salt mist. The adjoint automatic monitoring device includes: a wet candle method-based salt mist deposition rate acquisition unit, a single chip, a D/A conversion circuit, and a data acquisition module. The single chip is connected to the D/A conversion circuit. The D/A conversion circuit is connected to the wet candle method-based salt mist deposition rate acquisition unit. The single chip is configured to send a digital signal instruction. The D/A conversion circuit is configured to convert the digital signal instruction into an analog signal instruction and send the analog signal instruction to the wet candle method-based salt mist deposition rate acquisition unit. The data acquisition module is connected to a chloride ion selective electrode of the wet candle method-based salt mist deposition rate acquisition unit. The data acquisition module is configured to acquire a current value and a height variation output by the wet candle method-based salt mist deposition rate acquisition unit. The single chip is configured to calculate a deposition rate of salt mist based on the current value and the height variation. According to the present disclosure, a current value and a height variation of a solution in a trapping pool of the wet candle method-based salt mist deposition rate acquisition unit are acquired by the data acquisition module, and then the deposition rate of salt mist is calculated by the single chip. Real-time online monitoring of the deposition rate of salt mist is realized.

BRIEF DESCRIPTION OF THE DRAWINGS

To describe the technical solutions in embodiments of the present disclosure or in the prior art more clearly, the accompanying drawings needing to be used in the embodiments will be briefly described below. Apparently, the accompanying drawings in the following description show merely some embodiments of the present disclosure, and other accompanying drawings may be derived from these accompanying drawings by a person of ordinary skill in the art without creative efforts.

LIST OF REFERENCE NUMERALS

1—device top cover, 2—temperature and humidity sensor, 3—wet candle, 4—sealing plug, 5—trapping pool top cover, 6—sealing ring, 7—trapping pool, 8—chloride ion selective electrode, 9—liquid level height monitoring module, 10—M3×6 screw, 11—gasket, 12—lithium battery pack, 13—device base, 14—M4×

15 screw, 15—gauze, 16—switch, 17—circular connector, 18—data acquisition module, 19—M2.5×5 pan head screw, and 20—OLED display module.

DETAILED DESCRIPTION OF THE EMBODIMENTS

The technical solutions in the embodiments of the present disclosure will be clearly and completely described below with reference to the accompanying drawings in the embodiments of the present disclosure. Apparently, the described embodiments are merely a part rather than all of the embodiments of the present disclosure. All other embodiments derived from the embodiments in the present disclosure by a person of ordinary skill in the art without creative efforts shall fall within the protection scope of the present disclosure.

An objective of the present disclosure is to provide an adjoint automatic monitoring device and method for a deposition rate of salt mist to realize real-time online Monitoring parameter on a deposition rate of salt mist.

The embodiments of the present disclosure are further described in detail below with reference to the drawings.

Figure 1:
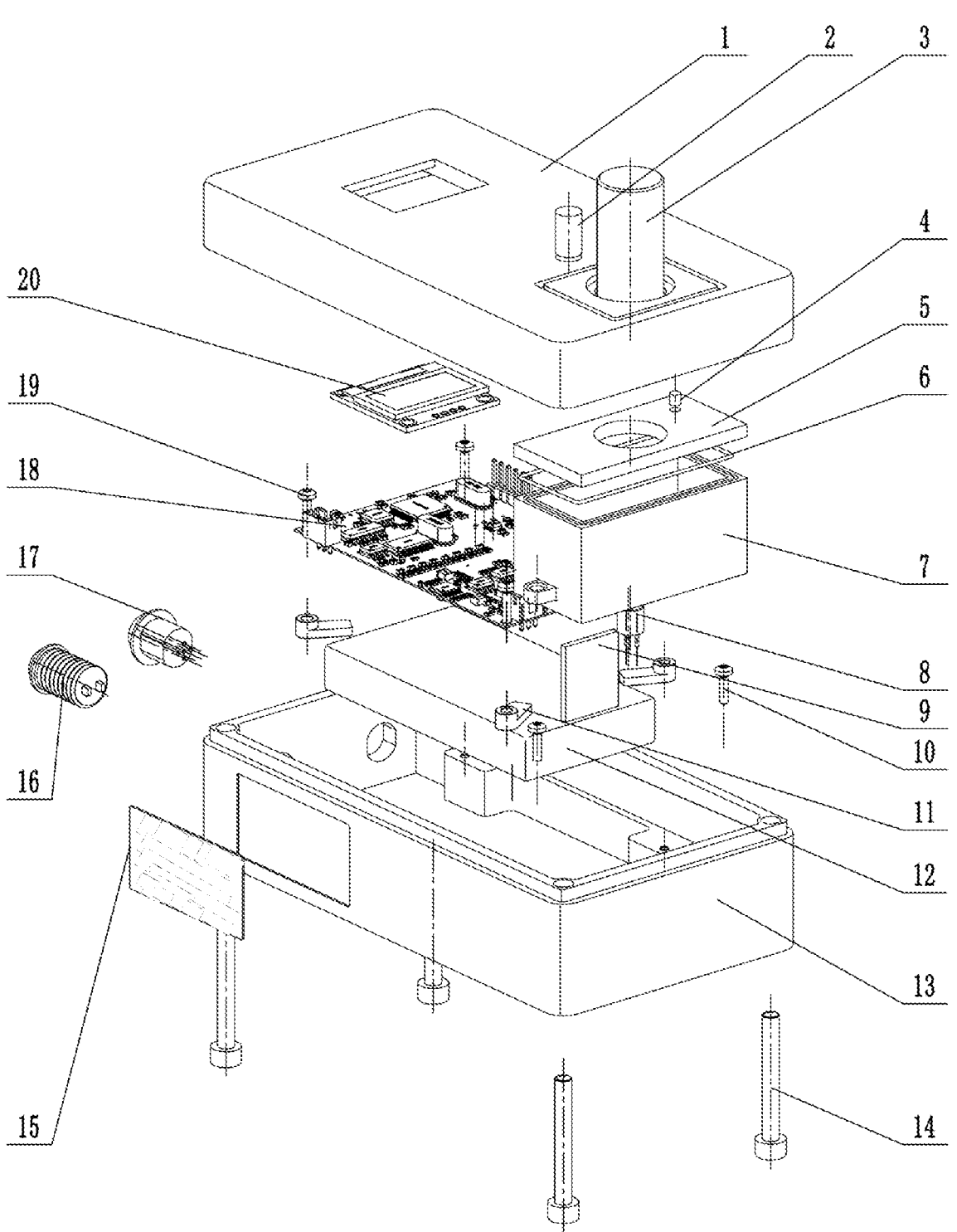
FIG. 1 is a structural schematic diagram of an adjoint automatic monitoring device for a deposition rate of salt mist provided by an embodiment of the present disclosure.

An adjoint automatic monitoring device for a deposition rate of salt mist provided in the present disclosure, as shown in FIG. 1, includes a device top cover 1, a temperature and humidity sensor 2, a wet candle method-based salt mist deposition rate acquisition unit 3, an OLED display module 20, a data acquisition module 18, a lithium battery pack 12, a device base 13, a switch 16, and a circular connector 17. The wet candle method-based salt mist deposition rate acquisition unit 3 is fixed to the device base 13 through an M3×6 screw; an acquisition portion of a gauze wound around a wet candle 3 is exposed through the device top cover 1 and covered with a metal mesh enclosure. The temperature and humidity sensor 2 is fixed to the device top cover 1 to monitor a temperature and a humidity of the wet candle part in real time. The OLED display module 20 is connected to the device top cover 1, and sealed and fixed by an epoxy resin. The data acquisition module 18 is connected to the device base 13, and the lithium battery pack 12 is fixed to the device base 13 by means of a fixing pin. The circular connector 17 and the switch 16 are fixed to the device base 13 through threaded connection.

Figure 2:
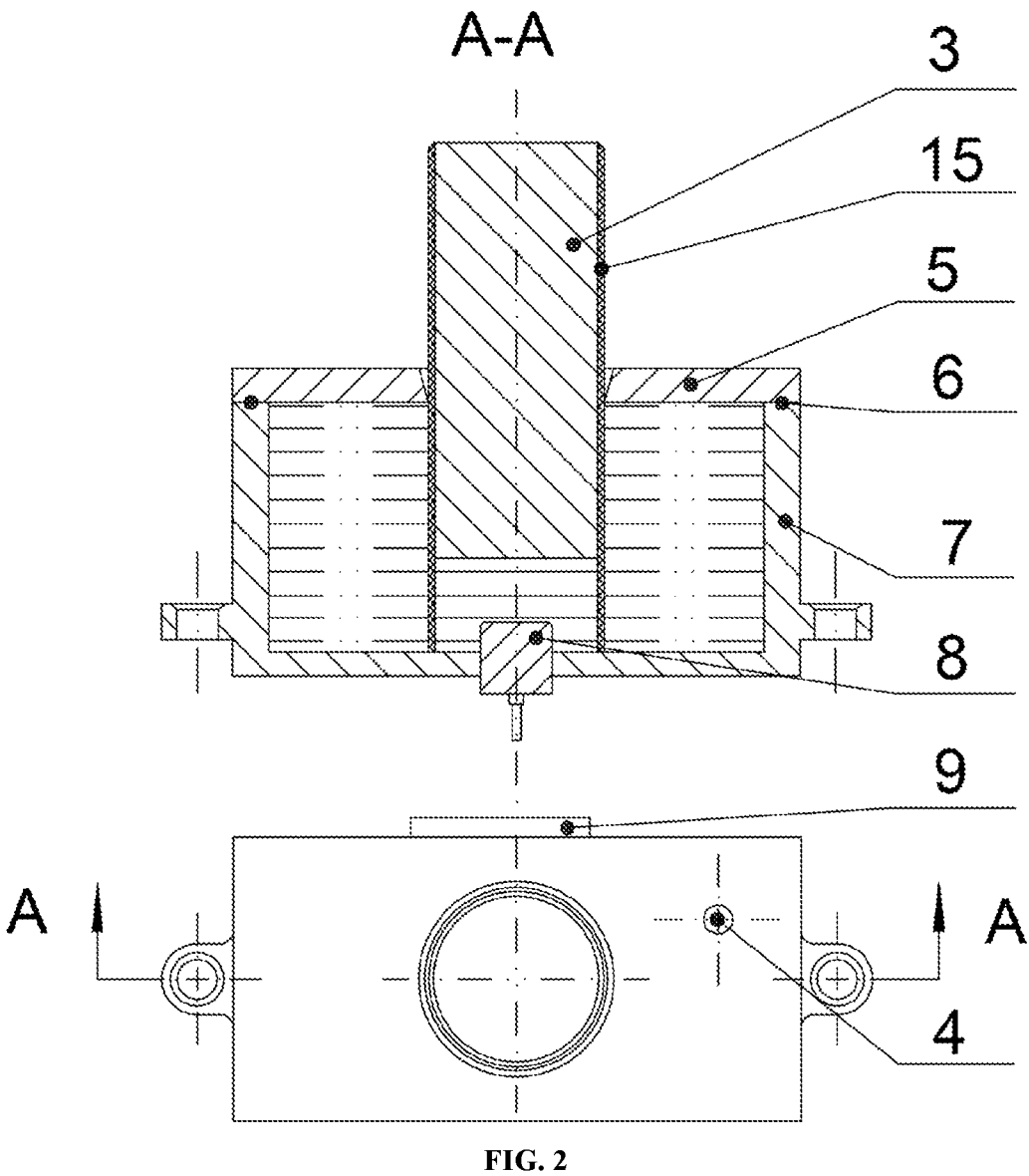
FIG. 2 is a structural schematic diagram of a wet candle method-based salt mist deposition rate acquisition unit provided by an embodiment of the present disclosure.

With reference to FIG. 2, the acquisition part for a deposition rate of salt mist by a wet candle method includes: the wet candle 3, the gauze 15, a trapping pool top cover 5, a sealing ring 6, a trapping pool 7, a chloride ion selective electrode 8, and a liquid level height detection module 9. The gauze is wound around the wet candle, and has one end fixed and the other end being a free end. The free end is placed into a solution in the trapping pool. Salt mist is deposited into the solution by means of the gauze. A variation of a current value in the solution is sensed by the electrode in real time. A taper hole is formed in the trapping pool top cover, which may facilitate free falling of the gauze and the deposition of salt mist. A sodium chloride solution (which is a mixed solution of sodium chloride and glycerol, with a sodium chloride concentration of 0.3-0.5 mg/ml in the mixed solution) is held in the trapping pool. After salt mist is deposited into the trapping pool, the current value in the trapping pool changes. The liquid level height detection module is directly mounted on an outer side of the trapping pool and is capable of realizing non-contact monitoring. A volatilization state of the solution in the trapping pool is monitored in real time, and an alarm state occurs when the content of the solution is lower than a set threshold. The solution may be added through a small hole formed in the trapping pool top cover.

Figure 3:
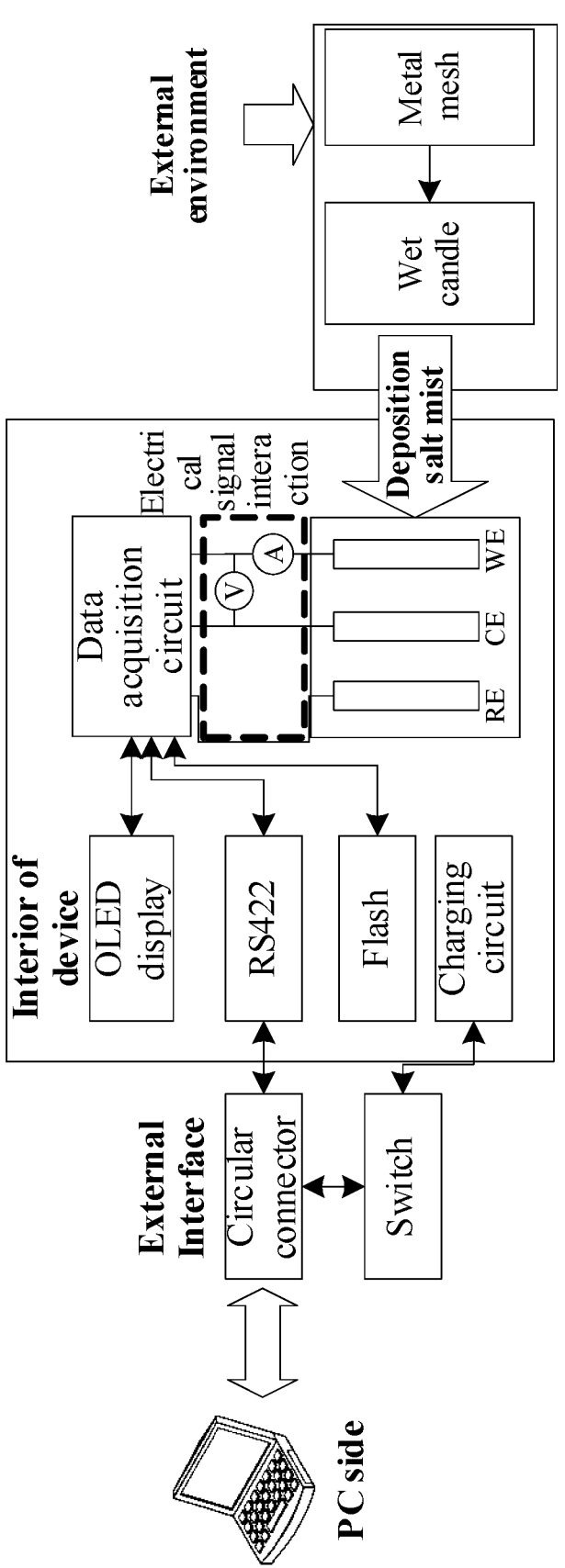
FIG. 3 is an overall block diagram of an adjoint automatic monitoring device for a deposition rate of salt mist provided by an embodiment of the present disclosure.
Figure 4:
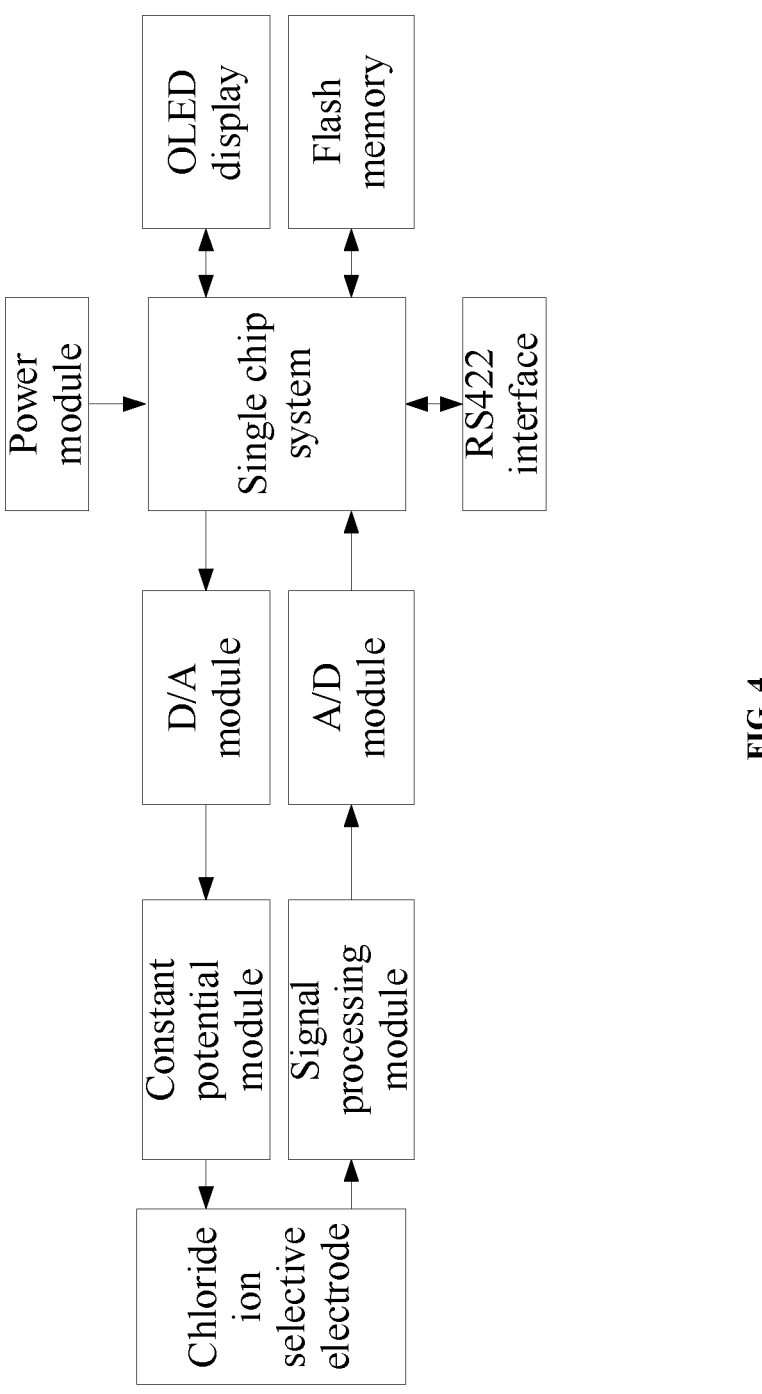
FIG. 4 is a functional block diagram of a data acquisition module provided by an embodiment of the present disclosure.

With reference to FIG. 3, the data acquisition and processing analysis part (i.e., the data acquisition circuit in FIG. 3) of the adjoint automatic monitoring device for a deposition rate of salt mist provided in the present disclosure mainly includes an analog/digital conversion part (i.e., a D/A conversion circuit), a single chip part (i.e., a single chip), a signal acquisition and uploading part (i.e., the data acquisition module), a clock unit, a data storage unit, and a power supply system. As shown in FIG. 4, a detection method is as follows: an excitation voltage signal needed by an electrode system is generated by the single chip and the D/A conversion circuit (corresponding to a D/A module in FIG. 4). The voltage signal is applied to an electrode module, and then the chloride ion selective electrode generates a corresponding detection signal. After the signal generated by the electrode is acquired by a signal processing module, the signal is converted into a digital signal by an A/D conversion circuit (corresponding to an A/D module in FIG. 4), and the digital signal is acquired by a single chip system and stored in a Flash module, and upload to a computer through an RS422 interface when needed. The OLED display module displays merely necessary information in the working process of the system.

Figure 5:
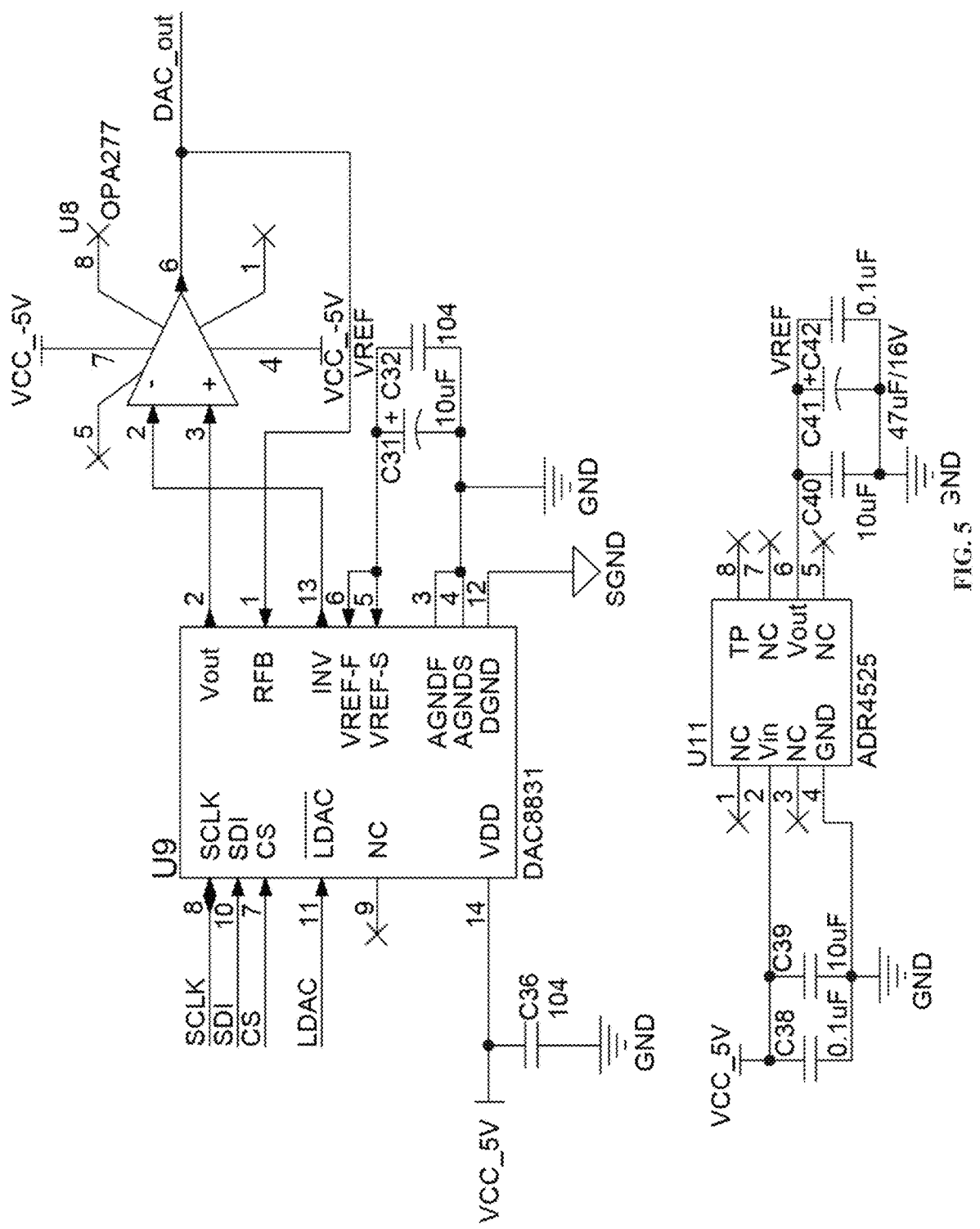
FIG. 5 is a schematic diagram of a D/A conversion circuit provided by an embodiment of the present disclosure.

With reference to the D/A conversion circuit shown in FIG. 5, after DAC8831 is in communication with the single chip through a serial peripheral interface (SPI), the single chip sends a digital signal instruction. The digital signal instruction is converted into an analog signal by the DAC, and the analog signal is output through DAC_out of OP277 and applied to the electrode.

Figure 6:
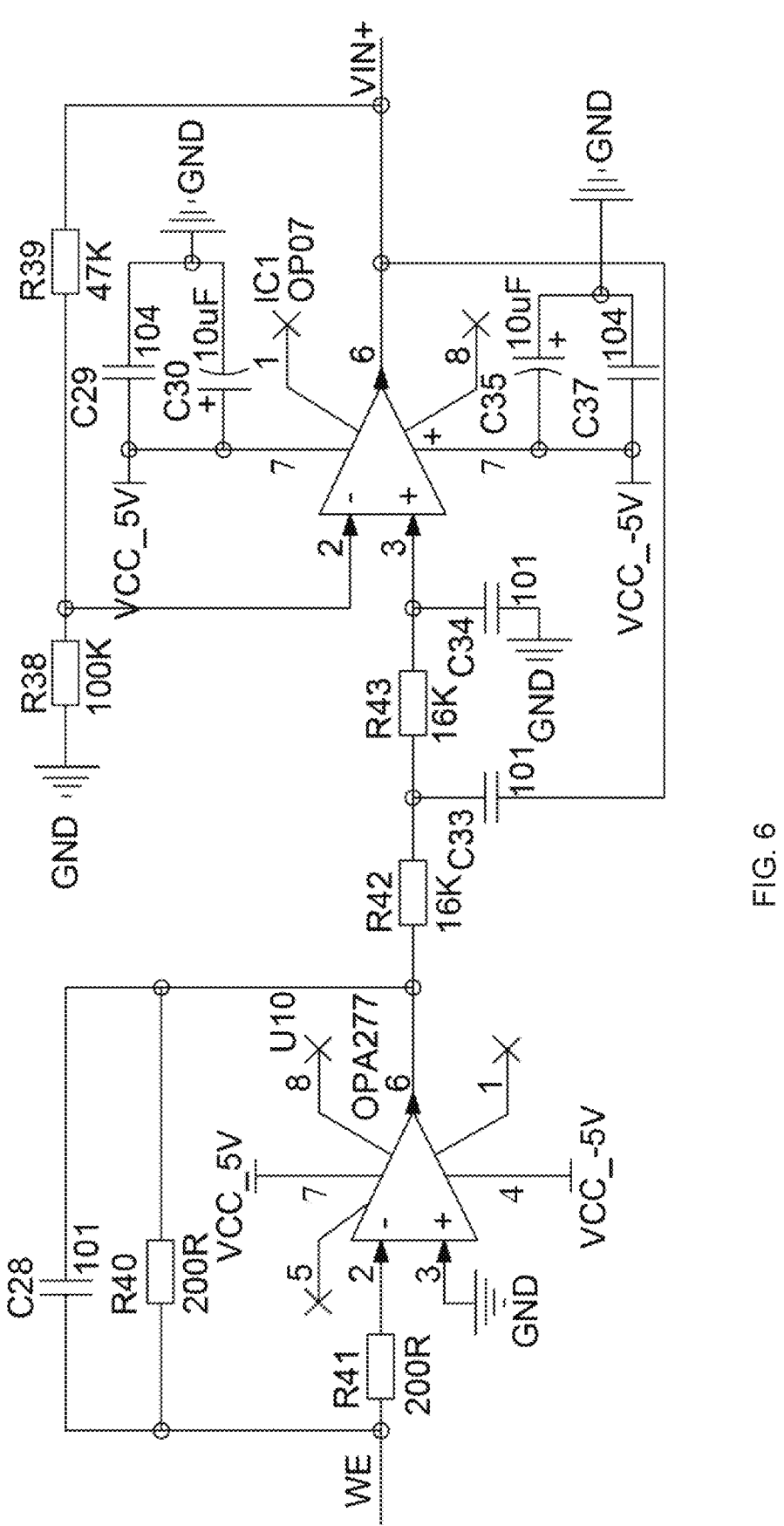
FIG. 6 is a schematic diagram of an I/V conversion circuit provided by an embodiment of the present disclosure.

With reference to the I/V conversion circuit shown in FIG. 6, a working electrode is connected to a left side of a resistor R41, and after I/V conversion, a voltage is output as $V_O = I_O * R40$. After I/V conversion by a resistor R40, the R40 may introduce a stray capacitance. Therefore, a second-order low-pass filter is designed to eliminate the influence of detection signal noise, and voltage VIN+ is output.

Figure 7:
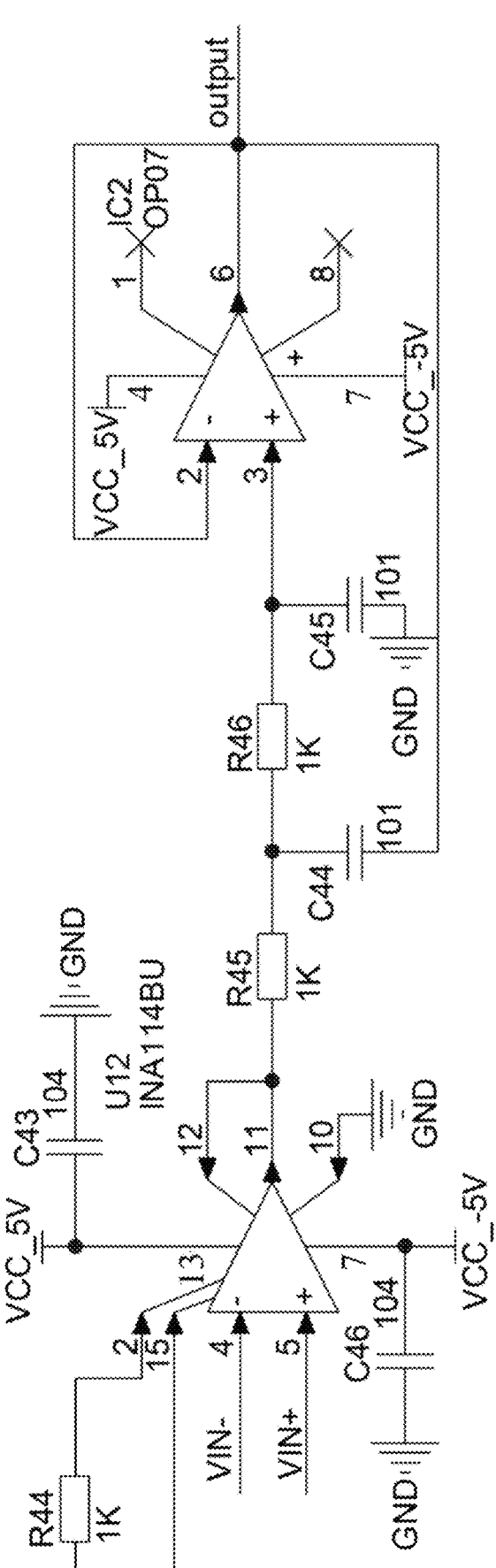
FIG. 7 is a schematic diagram of a two-stage amplifying circuit provided by an embodiment of the present disclosure.

With reference to a two-stage amplifying circuit shown in FIG. 7, INA114 design is adopted, with a gain factor $A = 1 + 50K\Omega / R44$. By experiments, a current output after the deposition of salt mist is generally at a uA level, and after I/V conversion of a preceding stage, the output voltage VIN+ is at an mV level. Gains are designed in the two-stage amplifying circuit as follows: A=10, and R44=5.6KΩ.

Figure 8:
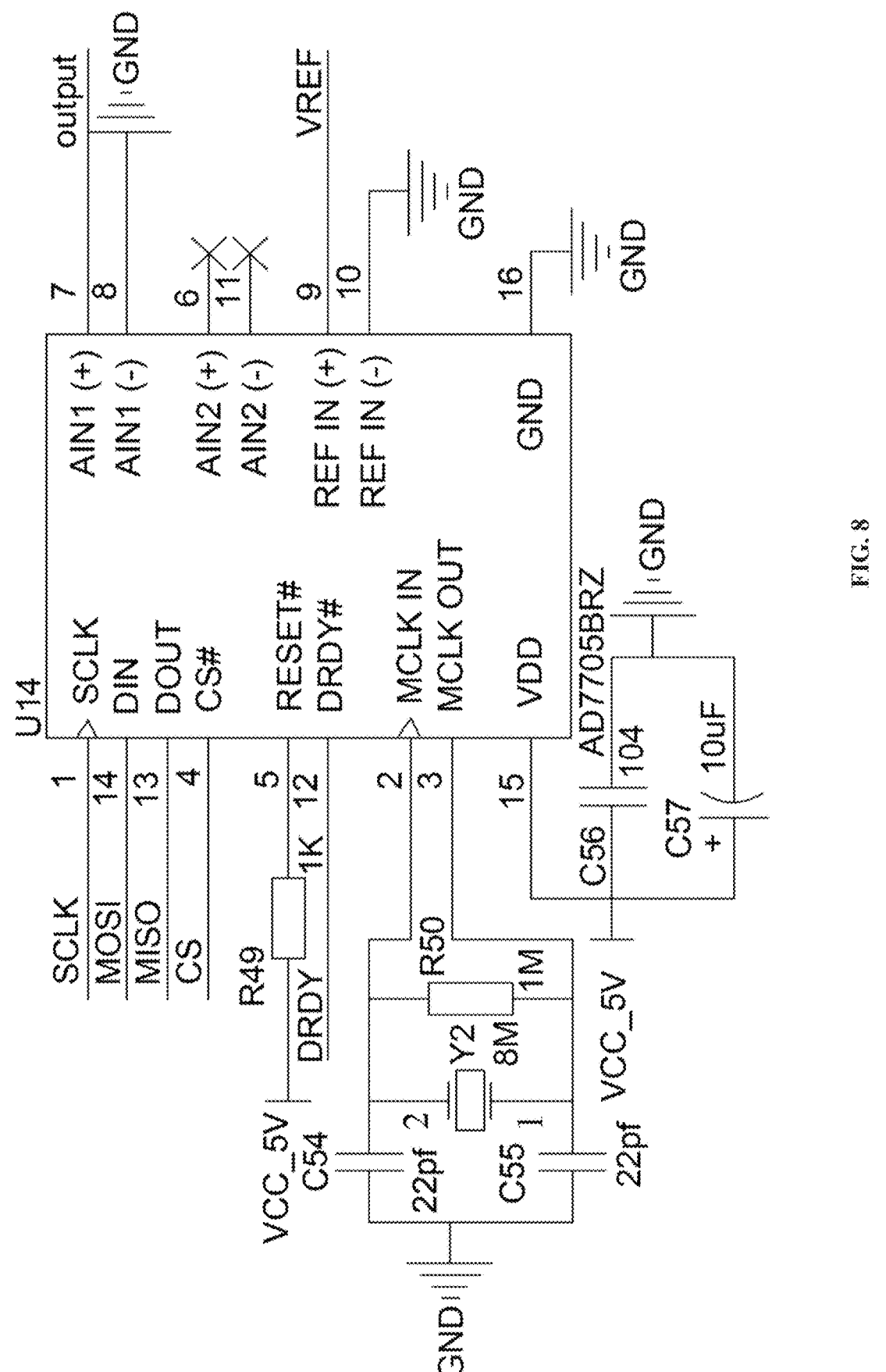
FIG. 8 is a schematic diagram of an A/D conversion circuit provided by an embodiment of the present disclosure.

With reference to AD7705 A/D conversion circuit shown in FIG. 8, the converted digital signal is transmitted to the single chip through SPI communication. The single chip may obtain a corresponding current value by converting the received digital signal. A salt mist deposition rate model curve may be obtained by calibrating mixed sodium chloride solutions at a plurality of concentrations, and the model is written in the single chip system so that a deposition rate of salt mist can be monitored online in real time.

In the circuit, R38, R39, R40, R41, R42, and R44 need to be low-temperature drift resistors. With resistors having a temperature coefficient of below 1 ppm and accuracy of above 1%, the accuracy of an analog acquisition circuit may be improved.

Figure 9:
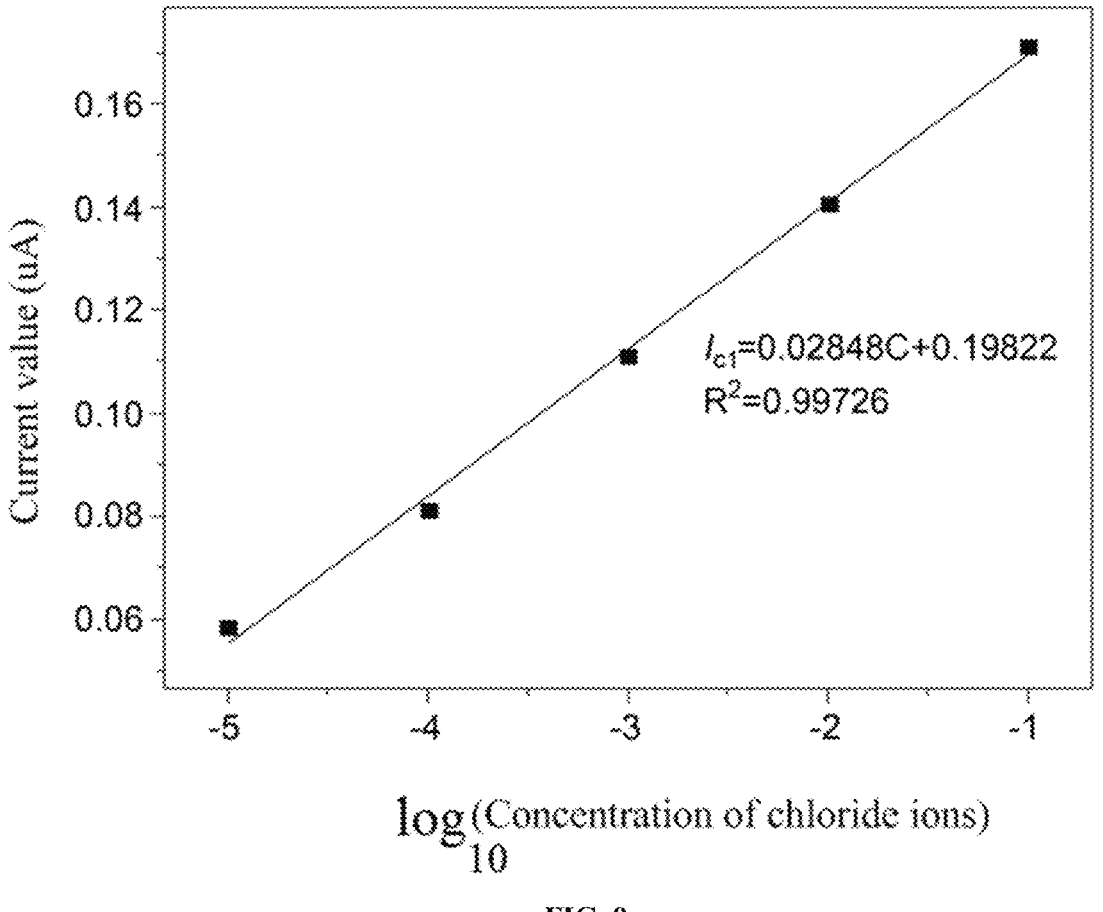
FIG. 9 is a schematic diagram of a calibration result provided by an embodiment of the present disclosure.

The device is calibrated separately by using sodium chloride solutions at concentrations of $10^{-1}$ mol/L, $10^{-2}$ mol/L, $10^{-3}$ mol/L, $10^{-4}$ mol/L, and $10^{-5}$ mol/L. Calibration data is as shown in FIG. 9, and a calibration result is obtained as $I_{cl}$=0.02848C+0.19822, where C represents of a concentration logarithm of chloride ions, i.e., C=$\log_{10}$ (concentration of chloride ions).

An exposed surface area may be calculated as A=3π with a volume of V=36 cm$^3$ of the solution in the trapping pool, an area S=12 cm$^2$, a height h=3 cm, a diameter of 1.5 cm of the wet candle, and a height of 2 cm of the exposed surface.

A liquid level height variation measured by the liquid level height detection module is Δh. A mass of chloride ions at a time may be calculated by the following formula:

$$m_t = 35.5 \times 10^{\frac{I_{cl}-0.19822}{0.02848}} \times 12 \times (3 - \Delta h),$$

and the deposition rate is calculated by the following formula:

$$S_d = \frac{m_t - m_0}{At},$$

where t is time (day), and $m_0$ is the mass (mg) of chloride ions in the prepared mixed solution of sodium chloride and glycerol in the trapping pool, and $$S_d = \frac{35.5 \times 10^{\frac{I_{cl}-0.19822}{0.02848}} \times 12 \times (3 - \Delta h) - m_0}{3\pi \times t} \left(\text{mg}/\left(\text{cm}^2 \cdot d\right)\right).$$

A real-time online monitoring method of the adjoint automatic monitoring device for a deposition rate of salt mist includes the following specific steps:

arrange a wet candle method-based salt mist deposition rate acquisition unit in an environment to be measured;

acquire a current value and a height variation of a solution in a trapping pool of the wet candle method-based salt mist deposition rate acquisition unit in real time;

calculate a concentration logarithm of chloride ions of the solution in the trapping pool by using a calibration relationship according to the current value, where the calibration relationship is used for characterizing a relationship between a current and a concentration of chloride ions; and calculate the deposition rate of salt mist based on the concentration logarithm of chloride ions and the height variation of the solution in the trapping pool.

The arranging a wet candle method-based salt mist deposition rate acquisition unit in an environment to be measured specifically includes:

(1) mount the prepared wet candle method-based salt mist deposition rate acquisition unit on a device base and fix it by using an M4×15 screw 14;

(2) mount a circular connector and a switch to the device base;

(3) mount a lithium battery and a circuit board on the device base, and fix the circuit board and the lithium battery by using M2.5×5 pan head screws 19;

(4) mount an OLED display module and a temperature and humidity sensing module on the device top cover and sealing them; and (5) connect adapters of all modules to the circuit board as designed and fix the device top cover and the base by using M4 screws.

Key information such as real-time concentration value of chloride ions, battery power, and mixed solution volume can be seen on the OLED display module. An RS422 data cable is connected to a transmission interface of the device, and an instruction is sent by upper computer software to upload data stored in Flash to the computer in the format of .txt. The data information includes key information such as a time, an amount of chloride ion deposition, a concentration, a temperature, and a humidity.

According to specific embodiments provided in the present disclosure, the present disclosure has the following technical effects:

1. According to the present disclosure, real-time online monitoring on an amount of deposition of salt mist in atmosphere can be realized with the wet candle method-based salt mist deposition rate acquisition unit, the data acquisition and uploading module, and the like. The deposition rates of salt mist can be recorded in real time, providing long-term data for studying the corrosion state of a structure.

2. The chloride ion selective electrode is employed in the present disclosure. The amount of deposition of chloride ions is directly obtained by measuring the current value variation of the electrode, whereby the deposition rate of chloride ions is calculated. There is no need for manual work in the whole measurement period, and efficient and rapid high-accuracy measurement can be realized. The recorded long-term data can be transferred to the computer through the RS422 serial port for specific analysis.

3. The real-time monitoring device for a deposition rate of salt mist in the present disclosure is capable of long-term real-time online monitoring without requiring manual work in the detection process. The device is small in size and can realize salt mist concentration monitoring in a narrow space. The device of the present disclosure clearly keeps ahead of a traditional detection method and an existing large-size monitoring device capable of realizing real-time monitoring.

The embodiments of the present disclosure are described above with reference to the accompanying drawings, but the present disclosure is not limited to the foregoing specific implementations. The foregoing specific implementations are merely illustrative rather than restrictive. Under the teaching of the present disclosure, those of ordinary skill in the art may make many variations without departing from the spirit of the present disclosure and the protection scope of the claims, and all such variations fall within the protection scope of the present disclosure.

What is claimed is:

1. An automatic monitoring device for a deposition rate of salt mist, comprising a wet candle method-based salt mist deposition rate acquisition unit, a single chip, a digital-to-analog (D/A) conversion circuit, and a data acquisition module;

wherein the single chip is connected to the D/A conversion circuit; the D/A conversion circuit is connected to the wet candle method-based salt mist deposition rate acquisition unit; the single chip is configured to send a digital signal instruction; the D/A conversion circuit is configured to convert the digital signal instruction into an analog signal instruction and send the analog signal instruction to the wet candle method-based salt mist deposition rate acquisition unit;

the data acquisition module is connected to a chloride ion selective electrode of the wet candle method-based salt mist deposition rate acquisition unit and the single chip separately; the data acquisition module is configured to acquire a current value and a liquid level height variation of a solution in a trapping pool output by the wet candle method-based salt mist deposition rate acquisition unit; and the single chip is configured to calculate a deposition rate of salt mist based on the current value and the liquid level height variation.

2. The automatic monitoring device for a deposition rate of salt mist according to claim 1, wherein the data acquisition module comprises a current-to-voltage (I/V) conversion circuit, a two-stage amplifying circuit, and an analog-to-digital (A/D) conversion circuit.

3. The automatic monitoring device for a deposition rate of salt mist according to claim 1, further comprising: a device base, a device top cover, a temperature and humidity sensor, a lithium battery pack, a switch, a circular connector, and an organic light-emitting diode (OLED) display module;

the wet candle method-based salt mist deposition rate acquisition unit is fixed to the device base; a gauze for depositing salt mist in an environment into a solution in the wet candle method-based salt mist deposition rate acquisition unit is exposed to the environment through a through hole formed in the device top cover and covered with a metal mesh enclosure;

the temperature and humidity sensor is disposed on the device top cover;

the lithium battery pack is disposed in the device base, and connected to the wet candle method-based salt mist deposition rate acquisition unit, the temperature and humidity sensor, the single chip, the D/A conversion circuit, the data acquisition module, and the OLED display module;

the switch and the circular connector are both disposed on a sidewall of the device base; the switch is connected to a power output terminal of the lithium battery pack; the circular connector is connected to the single chip through an RS422 serial port module and configured for connection with an external apparatus; and the OLED display module is disposed on the device top cover and connected to the single chip.

4. The automatic monitoring device for a deposition rate of salt mist according to claim 1, wherein the wet candle method-based salt mist deposition rate acquisition unit comprises a wet candle, the gauze, a trapping pool, the chloride ion selective electrode, and a liquid level height detection module;

the gauze has one end wound around the wet candle and the other end deposited into the solution in the trapping pool and serves for depositing the salt mist in the environment into the solution;

the chloride ion selective electrode has one end placed deep into the solution in the trapping pool and is configured to sense a current value of the solution in the trapping pool;

the liquid level height detection module is disposed on an outer side of the trapping pool and configured to sense a height variation of the solution in the trapping pool; and the current value and the height variation are used for calculating the deposition rate of salt mist.

5. The automatic monitoring device for a deposition rate of salt mist according to claim 4, wherein the trapping pool comprises a trapping pool body and a trapping pool top cover;

a sealing ring is disposed between the trapping pool body and the trapping pool top cover;

a taper hole is formed in the trapping pool top cover; and the other end of the gauze passes through the taper hole to be placed into the solution in the trapping pool body.

6. The automatic monitoring device for a deposition rate of salt mist according to claim 5, wherein an injection hole is further formed in the trapping pool top cover and sealed with a sealing plug.

7. The automatic monitoring device for a deposition rate of salt mist according to claim 1, wherein a formula for calculating the deposition rate of salt mist is as follows:

$$S_d = \frac{m_t - m_0}{At};$$
$$m_t = 35.5 \times 10^{\frac{I_{Cl}-0.19822}{0.02848}} \times 12 \times (3 - \Delta h);$$

wherein $S_d$ represents the deposition rate of salt mist, and $m_t$ a mass of chloride ions in the solution in the trapping pool at time t, $m_0$ an initial mass of chloride ions in the solution in the trapping pool, A an exposed surface area of the gauze, $I_{Cl}$ the sensed current value of the solution in the trapping pool, $\Delta h$ the height variation of the solution in the trapping pool, wherein a unit of $m_t$ and $m_0$ is mg, a unit of A is $cm^2$, a unit of $I_{Cl}$ is μA, and a unit of $\Delta h$ is cm.

8. An automatic monitoring method for a deposition rate of salt mist, comprising the following steps:

arranging a wet candle method-based salt mist deposition rate acquisition unit in an environment to be measured;

acquiring a current value and a height variation of a solution in a trapping pool of the wet candle method-based salt mist deposition rate acquisition unit in real time;

calculating a concentration logarithm of chloride ions of the solution in the trapping pool by using a calibration relationship according to the current value, wherein the calibration relationship is used for characterizing a relationship between a current and a concentration of chloride ions; and calculating the deposition rate of salt mist based on the concentration logarithm of chloride ions and the height variation of the solution in the trapping pool.

9. The automatic monitoring method for a deposition rate of salt mist according to claim 8, wherein the calibration relationship is as follows: $I_{Cl}=0.02848C+0.19822;$ wherein $I_{Cl}$ represents a sensed current value of the solution in the trapping pool, and C the concentration logarithm of chloride ions.

10. The automatic monitoring method for a deposition rate of salt mist according to claim 8, wherein a formula for calculating the deposition rate of salt mist is as follows:

$$S_d = \frac{m_t - m_0}{At};$$
$$m_t = 35.5 \times 10^{\frac{I_{Cl}-0.19822}{0.02848}} \times 12 \times (3 - \Delta h);$$

wherein $S_d$ represents the deposition rate of salt mist, and $m_t$ a mass of chloride ions in the solution in the trapping pool at time t, $m_0$ an initial mass of chloride ions in the solution in the trapping pool, A an exposed surface area of the gauze, $I_{Cl}$ the sensed current value of the solution in the trapping pool, $\Delta h$ the height variation of the solution in the trapping pool, wherein a unit of $m_t$ and $m_0$ is mg, a unit of A is $cm^2$, a unit of $I_{Cl}$ is μA, and a unit of $\Delta h$ is cm.

* * * * *